US009476892B2

(12) United States Patent
Beacham et al.

(10) Patent No.: US 9,476,892 B2
(45) Date of Patent: Oct. 25, 2016

(54) COMPOSITION AND METHOD FOR MEASURING THALLIUM INFLUX AND EFFLUX (71) Applicant: LIFE TECHNOLOGIES CORPORATION, Carlsbad, CA (US)

(72) Inventors: Daniel Beacham, Eugene, OR (US); Kyle Gee, Springfield, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/521,346

(22) Filed: Oct. 22, 2014

(65) Prior Publication Data
US 2015/0104823 A1 Apr. 16, 2015

Related U.S. Application Data (63) Continuation of application No. 12/738,257, filed as application No. PCT/US2008/079997 on Oct. 15, 2008, now abandoned.

(60) Provisional application No. 60/979,958, filed on Oct. 15, 2007.

(51) Int. Cl.
G01N 33/53 (2006.01)
G01N 33/84 (2006.01)
G01N 33/68 (2006.01)
C12Q 1/02 (2006.01)

(52) U.S. Cl.
CPC ............ *G01N 33/84* (2013.01); *C12Q 1/02* (2013.01); *G01N 33/6872* (2013.01); *G01N 2333/705* (2013.01)

(58) Field of Classification Search
None
See application file for complete search history.

(56) References Cited

U.S. PATENT DOCUMENTS

| 5,985,214 | A | 11/1999 | Stylli et al. |
| 6,057,114 | A | 5/2000 | Akong et al. |
| 6,162,931 | A | 12/2000 | Gee et al. |
| 6,171,780 | B1 | 1/2001 | Pham et al. |
| 2007/0172815 | A1 | 7/2007 | Weaver |
| 2010/0279314 | A1 | 11/2010 | Beacham et al. |

FOREIGN PATENT DOCUMENTS

| EP | 2201367 | 3/2013 |
| WO | 2009/052183 | 4/2009 |

OTHER PUBLICATIONS

CN 200880117916.8; Office Action and Search Report mailed Dec. 27, 2012.
Beacham, D. et al., "Potassium flux assay meets bacman technology", *Bioprobes*, vol. 55, Mar. 1, 2008; pp. 8-11.
Borman, S. et al., "Reducing Time to Drug Discovery", *C&E News*, vol. 77, No. 10, 1999; pp. 33-48.
EP12193171.1; European Search Report mailed 6 Pgs.
Gee, K. et al., "Measuring zinc in living cells. A new generation of sensitive and selective fluorescent probes", *Cell Calcium*, vol. 31, No. 5, 2002; pp. 245-251.
Hille, B. et al., "Potassium channels in myelinated nerve selective permeability to small cations", *Journal of general Physiology*, vol. 61, No. 6, 1973; pp. 669-686.
Hougaard, C. et al., "Selective positive moldulation of the SK3 and SK2 subtypes of small conductance Ca2+-activated K+ channels", *British Journal of Pharmacology*, vol. 151, 2007; pp. 655-665.
Karpen, J. et al., "Spectrophotometric detection of monovalent cation flux in cells: Fluorescence microscope measurement of acetylcholine receptor-mediated ion flux in PC-12 cells", *Analytical Biochemistry*, vol. 157, No. 2, 1986; pp. 353-359.
Moore, H. et al., "Direct spectroscopic studies of cation translocatoin by Torpedo acetylcholine receptor on a time scale of physiological relevance", *Proc. Natl. Acad. Sci. USA*, vol. 77, No. 8, 1980; pp. 4509-4513.
Niswender, C. et al., "A Novel Assay of Gi/o-Linked G Protein-Coupled Receptor Coupling to Potassium Channels Provides New Insights into the Pharmacology of the Group III Metabotropic Glutamate Receptors", *Molecular Pharmacology*, vol. 73, No. 4, 2008; pp. 1213-1224.
PCT/US08/79997; International Preliminary Report on Patentability mailed on Apr. 29, 2010.
PCT/US08/79997; International Search Report and Written Opinion mailed Jan. 28, 2009.
Weaver, C. David et al., "A thallium-sensitive, fluorescence-based assay for detecting & characterizing potassium channel modulators in mammalian cells", *Journal of Biomolecular Screening*, vol. 9, No. 8, 2004; pp. 671-677.

*Primary Examiner* — Michael Pak (57) ABSTRACT

The present invention relates to methods for detecting the activity of an ion channel in a cell. The methods comprise providing a loading buffer solution to a cell that has an ion channel. The loading buffer comprises at least one thallium indicator (e.g., an environmentally sensitive, luminescent dye) and a physiological concentration of chloride ions. The methods further comprise providing a stimulus buffer to the cell, wherein the stimulus buffer comprises thallium (e.g., thallium ions). Providing the stimulus buffer causes thallium influx into the cell through the ion channel. After providing the stimulus buffer, the luminescence (e.g., fluorescence) of the dye in the cell is detected. The luminescence of the dye can change in the presence or absence of thallium. The methods may be used to measure influx or efflux of thallium through an ion channel.

30 Claims, 2 Drawing Sheets

COMPOSITION AND METHOD FOR MEASURING THALLIUM INFLUX AND EFFLUX

CROSS REFERENCE TO RELATED APPLICATIONS

This is a continuation application claiming the right of priority under 35 U.S.C. §120 to U.S. patent application Ser. No. 12/738,257, filed Jul. 12, 2010, now abandoned, which is a national stage application claiming the right of priority under 35 U.S.C. §371 to International Patent Application No. PCT/US2008/079997, filed Oct. 15, 2008, which claims the benefit of U.S. Provisional Application No. 60/979,958, filed Oct. 15, 2007, under 35 U.S.C. §119, the disclosures of all of which are hereby expressly incorporated by reference in their entirety as though fully set forth herein.

BACKGROUND OF THE INVENTION

1. Field of the Invention

The present invention relates to methods for detecting the activity of an ion channel in a cell. The methods comprise providing a loading buffer solution to the cell, with the loading buffer comprises at least one environmentally sensitive thallium indicator (e g, luminescent dye) and chloride ions, and providing a stimulus buffer to the cell, wherein the stimulus buffer comprises thallium. Providing the stimulus buffer causes thallium influx into the cell through the ion channel. After providing the stimulus buffer, the luminescence (e.g., fluorescence) of the thallium indicator in the cell is detected, where the luminescence of the dye can change in the presence or absence of thallium.

2. Background of the Invention

High throughput screening (HTS) (e.g., HCS) of ion channels is currently limited by the efficiency of automated patch clamp instrumentation. The use of thallium influx as a surrogate indicator of potassium channel activity in clonal cell lines loaded with the calcium indicator BTC AM ester is now well-established (Weaver et al., *Journal of Biomolecular Screening* 2004; 9(8): 671-677). To date, the assays for monitoring ion channels use thallium (I), which selectively enters open potassium channels (Hille, *J. Gen. Physiol.* 1973; 61: 669-686) and binds to BTC, giving an optical readout of potassium channel activity. This method can be used to study the activation and/or inhibition of ion channels with drugs tested in HTS mode from a compound library.

The current methods, however, have significant drawbacks. Namely, thallium chloride is poorly soluble and will precipitate out of solution at a concentration of about 4.5 mM or greater. Thus, the buffers used for current methods must be essentially free of chloride to prevent TlCl from precipitating out of solution to generate data. The current methods, therefore, require additional steps of washing and removal of buffers in which cells are normally grown in culture (e.g., chloride containing buffers). Moreover, because chloride is absent in these assays, the assays can arguably be seen as not approximating physiological conditions.

SUMMARY OF THE INVENTION

The present invention relates to methods for detecting the activity of an ion channel in a cell. The methods may be used to measure influx or efflux of thallium through an ion channel. In general, the methods comprise providing a loading buffer solution to the cell, with the loading buffer comprises at least one environmentally sensitive thallium indicator (e.g., a luminescent dye, such as a fluorescent dye) and chloride (e.g., chloride ions), and providing a stimulus buffer to the cell, wherein the stimulus buffer comprises thallium. The loading buffer can include a physiological concentration of chloride ions. Providing the stimulus buffer can cause thallium influx into the cell through the ion channel. After providing the stimulus buffer, the luminescence (e.g., fluorescence) of the dye in the cell is detected, where the luminescence of the dye can change in the presence or absence of thallium.

In one aspect, a method for detecting the activity of an ion channel in a cell is provided. The method includes a) providing a cell with an ion channel; b) providing a loading buffer solution to the cell, the loading buffer solution comprising a thallium indicator and a physiological concentration of chloride ions; c) providing a stimulus buffer to the cell, wherein the stimulus buffer comprises thallium, and wherein providing the stimulus buffer causes thallium influx into the cell through the ion channel; and d) detecting the thallium indicator. Certain methods of the invention further include quantifying the level of detected thallium. For example, the level of thallium may be determined by measuring at least one optical property of the thallium indicator in response to thallium influx (e.g., intensity, polarity, frequency, or optical density). The detection method may be light microscopy, confocal microscopy, fluorescence microscopy or spectrophotometry.

In another aspect, a method for detecting the activity of an ion channel in a cell is provided that includes a) contacting a cell with a loading buffer solution, wherein the cell comprises an ion channel, and wherein the loading buffer solution comprises a thallium indicator and a physiological concentration of chloride ions; b) providing a stimulus buffer to the cell, wherein the stimulus buffer comprises thallium, and wherein providing the stimulus buffer causes thallium influx into the cell through the ion channel; and c) detecting the thallium indicator.

In yet another aspect, a method for detecting the activity of an ion channel in a cell is provided that includes a) loading a cell with thallium, wherein the cell comprises an ion channel; b) providing a solution to the cell, the solution comprising a thallium indicator and a physiological concentration of chloride ions; c) stimulating the ion channel of the cell, such as to cause efflux of thallium through the ion channel; and d) detecting the thallium indicator. The method can further include washing the cells to remove excess thallium. The ion channel of the cell used in the method may be impermeable to the thallium indicator.

The methods of the invention may be used to analyze various types of ion channels, including potassium ion channels, ion channels that are linked to receptors, channel-linked receptors, and ion transporters. The ion channel may be a ligand- or voltage-gated ion channel, a stretch-activated cation channel, or a selective or non-selective cation channel.

The methods of the invention may be used to analyze various types of cells, including bacterial, yeast, plant, and animal cells (e.g., mammalian cells). The cell may be a neuron, cardiac cell, cancer cell, a smooth muscle cell, or an immortalized cell. The cell may include potassium channel. The ion channel may be permeable to thallium ions.

In yet another aspect, the invention provides a loading buffer solution that includes a thallium indicator. Numerous types of thallium indicators may be used in the practice of the invention. The thallium indicators may be a hydrophilic or hydrophobic compound that can associate with thallium (e.g., thallium within the cell or buffer to detect extracellular levels of thallium) and can have an optical property that changes in the presence or absence of thallium. For example, the thallium indicator can exhibit an increase in fluorescence when associated with a thallium ion, or the thallium indicator can exhibit a change in the optical density inside the cell when associated with a thallium ion. The thallium indicator can be an environmentally sensitive fluorescent dye or a non-fluorescent compound (e.g., a compound that associates with thallium to form a precipitate or a colored product, such as iodide, bromide, and chromate). The thallium indicator can be a fluorescent compound that exhibits a fluorescence intensity change of 25% or greater in the Thallium Sensitivity Assay. Compounds that test positive in the Thallium Sensitivity Assay (see, Example 3) and may be utilized in the practice of the invention include fluorescent compounds that are sensitive to monovalent or divalent cations (e.g., $Zn^{2+}$ or $Ca^{2+}$ indicators). Exemplary compounds that test positive in the Thallium Sensitivity Assay may include a xanthene moiety (e.g., FluoZin 1, FluoZin 2, FluoZin 3, FluoZin 4, Red Fluo-4FF, Magnesium Green, Phen Green, RhodZin-3, or a derivative or salt thereof); a coumarin moiety (e.g., BTC or APTRA-BTC or a derivative or salt thereof); a benzofuran moiety (e.g., Mag-Fura Red or a derivative or salt thereof), a naphthalene moiety; or a crown ether moiety. The thallium indicator can exhibit a decrease in fluorescence intensity in the presence of thallium ions (e.g., ANTS, Fluo-4, Fluo-3, PBFI, Phen Green, APTRA-BTC or Mag-Fura Red or a derivative or salt thereof) or can exhibit an increase in fluorescence in the presence of thallium ions (e.g., Magnesium Green, Fluo-4FF, FluoZin-1 or FluoZin-2, RhodZin-3, or a derivative or salt thereof). In some embodiments, the thallium indicator may be ANTS, Fluo-4, Fluo-3, PBFI, Phen Green, Magnesium Green, Mag-Fora Red Fluo-4FF, FluoZin-1 and FluoZin-2, RhodZin-3, or a derivative or salt thereof.

The thallium indicator may include an acetoxymethyl ester moiety. For example, the thallium indicator may be an acetoxymethyl (AM) ester derivative of a compound selected from the group consisting of ANTS, Fluo-4, Fluo-3, PBFI, Phen Green, Magnesium Green, Mag-Fura Red, Fluo-4FF, FluoZin-1, RhodZin-3 and FluoZin-2.

The provided methods can utilize a loading buffer solution that comprises a physiological concentration of chloride ions (e.g., greater than about 2 mM; or about 5 mM to about 20 mM; or about 20 mM to about 100 mM; or about 50 mM to about 150 mM). The source of the chloride may be in the form of a salt, such as NaCl or KCl.

The provided methods can utilize a stimulus buffer that comprises thallium. The thallium may be may be in the form or a salt, which may be soluble in the loading buffer solution. For example, the thallium salt may be $Tl_2SO_4$, $Tl_2CO_3$, TlCl, TlOH, TlOAc, or $TlNO_3$. The stimulus buffer can include thallium at a concentration of less than about 4.5 mM; or less than about 4.0 mM; or less than about 3.0 mM; or the thallium concentration can range from about 0.1 to about 2.0 mM. In certain embodiments, the stimulus buffer can include thallium (e.g., thallium ions) at a concentration of about about 0.1 mM to about 2 mM and the loading buffer may include chloride ions at a concentration of about 10 mM to about 150 mM. In other embodiments, the concentration of thallium may be about 2 mM to about 5 mM and the loading buffer comprises chloride ions at a concentration of about 10 mM to about 150 mM. In yet other embodiments, thallium is at a concentration of about 5 mM to about 20 mM and the loading buffer comprises chloride ions at a concentration of about 10 mM to about 150 mM.

The cells may, optionally, be washed after the loading buffer solution is provided to the cells (e.g., to remove excess thallium indicator). In certain embodiments, the cells are not washed, and a quencher may be added to the loading buffer solution. In this case, the quencher may be substantially not cell permeant. Examples of quenchers include tartrazine, amaranth, acid red 37, congo red, trypan blue, brilliant black, or a combination of these quenchers.

The methods of the invention can include stimulating the ion channel with a stimulus (e.g., a ligand that binds to the ion channel, a channel-linked receptor, or an electrical stimulus). The stimulus may be a G-protein coupled receptor agonist capable of activating GIRK potassium ion channels to allow thallium influx. Alternatively, or in addition, the stimulus may be nicotine, acetylchloline, muscarine, carbamyline, or a GIRK potassium ion channel activator. The stimulus may be or include a composition that will cause depolarization of the ion channel (e.g., ionophores, valinocmycin, or potassium salts) or a composition that includes channel rhodopsin, halorhodopsin, or quantum dot nanocrystals.

In yet another aspect, kits are provided for detecting the activity (e.g., thallium influx or efflux) of an ion channel in a cell. Certain kits (e.g., kits for detecting thallium ion influx) can include a loading buffer solution, wherein the loading buffer solution comprises a thallium indicator and a physiological concentration of chloride ions; and a stimulus buffer, wherein the stimulus buffer comprises thallium, and wherein the stimulus buffer causes thallium influx into the cell through the ion channel. Certain kits (e.g., kits for detecting thallium ion efflux) may include a thallium loading solution, wherein the solution comprises thallium; and a solution (e.g., a buffer solution) that comprises a thallium indicator and a physiological concentration of chloride ions.

In yet another aspect, solutions for detecting the activity of an ion channel in a cell comprising: a) a thallium indicator; b) a physiological concentration of chloride ions; and c) thallium. The thallium concentration of the solution may be <4.5 mM or about 0.1 mM to about 4 mM; or about 0.1 mM to about 2 mM. The chloride ion concentration of the solution is about 10 mM to about 150 mM or about 50 mM to about 150 mM.

The present invention solves problems associated with current thallium influx and efflux assays by providing methods of monitoring ion channels where at least some of the buffers comprise a physiological concentration of chloride ions.

DETAILED DESCRIPTION OF THE INVENTION

Before describing the present invention in detail, it is to be understood that this invention is not limited to specific compositions or process steps. It should be noted that, as used in this specification and the appended claims, the singular form "a", "an" and "the" include plural references unless the context clearly dictates otherwise. It also should be noted that the term "about", when used to describe a numerical value, shall encompass a range up to ±15% of that numerical value, unless the context clearly dictates otherwise.

The present invention relates to methods for detecting the activity of an ion channel in a cell. As used herein, the term "cell" is intended to mean one or more cells. The cells can be in any environment, provided that the loading and stimulus buffers can be applied to the cells. In one embodiment, the cell is in an in vitro environment and the methods are performed using well-known cell culture techniques. In a more specific embodiment, the cell is in a cell culture suspension. In another specific embodiment, the cell is in a cell adhesion culture.

The methods of the present invention can be practiced on any cell, provided the cell possesses/expresses an ion channel that is permeable to thallium. Examples of ion channels include but are not limited to potassium ion channels, ion channels that are linked to receptors, e.g., GIRK, and channel-linked receptors, e.g., GPCR, and ion transporters, e.g., glutamate transporters. The cells may normally possess or express the ion channels, or the ion channels may be introduced into the cells using well-known transfection and transformation techniques. Methods are provided for assaying cells expressing native levels of ion channel (e.g., non-engineered cells) and for assaying cells that have been modified (e.g., engineered) by the practitioner to include an ion channel.

The methods are not limited to a particular type of ion channel, provided that the channel is permeable to thallium. Thus, the types of ion channels that can be used in the methods of the invention include, but are not limited to, ligand- or voltage-gated, stretch-activated cation channels, selective or non-selective cation channels.

Types of ligand-gated non-selective cation channels include, but are not limited to, acetylcholine receptors, glutamate receptors such as AMPA, kainate, and NMDA receptors, 5-hydroxytryptamine-gated receptor-channels, ATP-gated (P2X) receptor-channels, nicotinic acetylcholine-gated receptor-channels, vanilloid receptors, ryanodine receptor-channels, $IP_3$ receptor-channels, cation channels activated in situ by intracellular cAMP, and cation channels activated in situ by intracellular cGMP.

Types of voltage-gated ion channels include, but are not limited to, $Ca^{2+}$, $K^+$, and $Na^+$ channels. The channels can be expressed exogenously or endogenously. The channels can be stably or transiently expressed in both native or engineered cell lines.

Types of $K^+$ channels include, but are not limited to, KCNQ1 (KvLOT1), KCNQ2, KCNQ3, KCNQ4, KCNQ5, HERG, KCNE1 (IeK, MinK), Kv1.5, Kir 3.1, Kir 3.2, Kir 3.3, Kir 3.4, Kir 6.2, SUR2A, ROMK1, Kv2.1, Kv1.4, Kv9.9, Kir6, SUR2B, KCNQ2, KCNQ3, GIRK1, GIRK2, GIRK3, GIRK4, h1K1, KCNA1, SUR1, Kv1.3, hERG, intracellular calcium-activated $K^+$ channels, rat brain (BK2); mouse brain (BK1) and the like. Additional ion channels are disclosed in Conley, E. C. and Brammer, W. J., The Ion Channel, Factsbook IV, Academic Press, London, UK, (1999), which is incorporated herein by reference.

Types of $Na^+$ channels include, but are not limited to, rat brain I, II and III, human II and the like.

Types of $Ca^{2+}$ channels include, but are not limited to, human calcium channel $\alpha_1$, $\alpha_2$, $\beta$ and/or $\gamma$ subunits, the ryanodine receptor (RyR) and the inositol 1,4,5-triphosphate receptor ($IP_{3R}$), rabbit skeletal muscle $\alpha_1$ subunit, rabbit skeletal muscle $\alpha_2$ subunit, rabbit skeletal muscle p subunit, rabbit skeletal muscle $\gamma$ subunit and the like.

The methods of the present invention can also be applied to indirectly measure the activity of channel-linked receptors and signal transduction systems. Channel activity may be modulated from interactions between receptor subunits with ion channels, e.g., GPCR $\beta$-$\gamma$ subunits and GPCR-linked $K^+$ channels, e.g., GIRKs, or by changes in the concentrations of messenger molecules such as calcium, lipid metabolites, or cyclic nucleotides which, modulate the ion channel activity.

Accordingly, the present invention provides methods for monitoring, detecting and/or measuring the activity of intracellular events that are known to cause changes in ion channel permeability. Intracellular activity can include, but is not limited to protein phosphorylation or de-phosphorylation, up-regulation or down-regulation of transcription, internal calcium influx or efflux, cellular division, cellular apoptosis, receptor dimerization and the like. Thus, the measurement or detection of such intracellular events can also serve as a indirect detection or measure of the ion channels, if so desired.

In addition, G-coupled protein receptors may also be utilized in the present invention. Examples of G-coupled protein receptors include, but are not limited to, muscarinic acetylcholine receptors (mAChR), adrenergic receptors, serotonin receptors, dopamine receptors, angiotensin receptors, adenosine receptors, bradykinin receptors, metabotropic excitatory amino acid receptors and the like.

Another type of indirect assay of the invention involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in an increase or decrease in the cAMP or cGMP levels of the cytoplasm. Furthermore, some cyclic nucleotide-gated ion channels, e.g., rod photoreceptor cell channels and olfactory neuron channels are known to be permeable to cations upon activation by binding of cAMP or cGMP. Thus, in accordance with the methods of the present invention, a change in cytoplasmic ion levels, caused by a change in the amount of cyclic nucleotide activation of photo-receptor or olfactory neuron channels, can be used to determine the function of receptors that cause a change in cAMP or cGMP levels when activated. In one embodiment, a reagent that increases or decreases intracellular nucleotide levels is added to the cell, e.g., forskolin, prior to the addition of a receptor-activating compound. For example, if activation of a receptor is known or suspected to result in a decrease in cyclic nucleotide levels, forskolin, which is known to increase intracellular levels of nucleotide levels, may be added to the cells prior to adding a receptor-activating compound to the cells in the assay.

Cells used for this type of assay can be generated by co-transfection of a host cell with DNA encoding an ion channel, such as hERG, and DNA encoding a channel-linked receptor which, when activated, cause a change in cyclic nucleotide levels in the cytoplasm.

Receptors for use in the invention, include, but are not limited to, muscarinic receptors, e.g., human M2, rat M3, human M4, human M5, and the like. Other receptors include, but are not limited to, neuronal nicotinic acetylcholine receptors, e.g., the human $\alpha_2$, human $\alpha_3$, and human $\beta_2$, human $\alpha_5$, subtype rat $\alpha_2$ subunit, rat $\alpha_3$ subunit, rat $\alpha_4$ subunit, rat α$_5$ subunit, chicken α$_7$ subunit, rat β$_2$ subunit, rat β$_3$ subunit rat β$_4$ subunit, combinations of the rat α a subunits, rat NMDAR1 receptor, mouse NMDA el receptor, rat NMDAR2A, NMDAR2B and NMDAR2C receptors, rat metabotropic mGluR1 receptor, rat metabotropic mGluR2, mGluR3 and mGluR4 receptors, rat metabotropic mGluR5 receptor and the like. Other receptors include, but are not limited to, adrenergic receptors, e.g., human beta 1, human alpha 2, hamster beta 2, and the like. Still other receptors include, but are not limited to, dopamine receptors, serotonin receptors and serotonin receptors, e.g., human D2, mammalian dopamine D2 receptor, rat dopamine receptor, human 5HT1a, serotonin 5HT1C receptor, human 5HT1D, rat 5HT2, rat 5HT1c and the like.

The term "ion channel" also includes ion transporters. Examples of ion transporters include, but are not limited to, neurotransmitter ion transporters, e.g., dopamine ion transporter, glutamate ion transporter or serotonin ion transporter, sodium-potassium ATPase, proton-potassium ATPase, sodium/calcium exchanger, and potassium-chloride ion cotransporter.

Types of cells that can be used in the methods of the present invention include, but are not limited to, bacterial cells, yeast cells, plant cells and animal cells. Examples of animal cells that can be used in the present invention include but are not limited to insect cells, avian cells, and mammalian cells. Other examples of cells that can be examined using the methods of the invention are neurons, cardiac cells, cancer cells, smooth muscle cells, and the like. In certain embodiments, the cells may be immortalized cells.

Methods to determine activity of an ion channel in a cell are provided and may be used to detect influx or efflux of thallium (e.g., thallium ions) though an ion channel of a cell. In one aspect, a method of determining influx of thallium through an ion channel is provided. In general, methods to evaluate thallium influx involve contacting a cell (or a solution of cells) with a loading buffer solution that includes a thallium indicator and a physiological concentration of chloride ions. A stimulus buffer that includes thallium then is added to the cell to cause thallium influx into the cell through the ion channel. Detection of the thallium indicator upon stimulation of the cell provides information about the activity of the ion channel. In certain embodiments, an optical property of the thallium indicator is detected.

To perform the methods of the present invention, a loading buffer solution is provided to the cells. The loading buffers used in the present invention comprise an environmentally sensitive agent and chloride ions. As used herein, an "environmentally sensitive agent" is a compound, such as a dye, where at least one property (e.g., optical property) of the compound changes in response to one aspect of its immediate environment. In particular, at least one optical property of the agents used in the present invention should be sensitive to thallium concentrations. Thus, in one aspect, an environmentally sensitive agent may be a thallium sensitive agent. A "thallium sensitive agent" or "thallium indicator," as used herein, is a compound having at least one optical property, such as a dye, where at least one property (e.g., optical property) of the compound changes in response to the presence or absence of thallium (e.g., thallium ions).

The loading buffer may also include additional components, such as but not limited to, serum albumin, transferrin, L-glutamine, lipids, antibiotics, β-mercaptoethanol, vitamins, minerals, ATP and similar components may be present. The loading buffer may also include at least one inhibitor of organic ion transport, such as, but not limited to, benzbromarone, probenecid allopurinol, colchicine and sulfinpyrazole. Examples of vitamins that may be present include, but are not limited to vitamins A, B$_1$, B$_2$, B$_3$, B$_5$, B$_6$, B$_7$, B$_9$, B$_{12}$, C, D$_1$, D$_2$, D$_3$, D$_4$, D$_5$, E, tocotrienols, K$_1$ and K$_2$. Additional components to improve solubilization of the thallium indicator, such as surfactants (e.g., polyoxyalkylene ethers, such as PLURONIC F127, P85, and the like, available from BASF Corporation, Mount Olive, N.J.) or POWERLOAD (available from Invitrogen Corporation, Carlsbad, Calif.) may be included in the loading buffer. One of skill in the art can determine the optimal concentration of minerals, vitamins, ATP, lipids, essential fatty acids, etc., for use in a given culture. The concentration of supplements may, for example, be from about 0.001 μM to about 1 mM or more. Specific examples of concentrations at which the supplements may be provided include, but are not limited to about 0.005 μM, 0.01 μM, 0.05 μM, 0.1 μM, 0.5 μM, 1.0 μM, 2.0 μM, 2.5 μM, 3.0 μM 4.0 μM, 5.0 μM, 10 μM, 20 μM, 100 μM, etc. Agents used to assist and retain dye loaded into cells may also be used, such as probenecid in a variety of possible formulations, including a water soluble form or a base-soluble form prepared and used at concentrations ranging from 100 micromolar to 10 millimolar.

Thallium sensitive agents are employed as an indicator of the flux of thallium across the cell membrane and are sufficiently sensitive so as to produce detectable changes in at least one optical property in response to changes in the concentration of the thallium ions in the cell cytoplasm. Types of thallium sensitive agents that can produce a detectable signal include, but are not limited to, fluorescent compounds and non-fluorescent compounds.

Thallium indicators that may be used in the practice of the invention include compounds having sensitivity to monovalent ions or divalent ions. For example, a thallium indicator may have sensitivity to monovalent ions, such as Li$^+$, Na$^+$, K$^+$, Rb$^+$ Ag$^+$. Au$^+$, or sensitivity to divalent ions, such as Zn$^{+2}$, Ca$^{+2}$, Mg$^{2+}$, Hg$^{2+}$, Pb$^{2+}$, Cd$^{2+}$, Fe$^{2+}$, and Ni$^{2+}$.

The type of assay and/or ion channel being evaluated can be an important factor in determining which thallium indicator is used. For certain applications, a thallium indicator having a high sensitivity to thallium may be required. In other applications, however, lower sensitivity thallium indicators may be used. Thallium indicators with varying sensitivities to thallium ions are provided.

In certain embodiments, the thallium indicator has sensitivity to thallium (I) ions. A compound's sensitivity to thallium (I) ions may be assessed in a number of different ways. One approach is to use a fluorescence-based sensitivity assay. In general, a thallium sensitivity assay may involve combining a compound, as described herein, at a given concentration with varying amounts thallium ions in buffer and monitoring the change in the compound's fluorescence intensity as a function of increasing thallium ion concentration. Thallium sensitivity may be evaluated using the Thallium Sensitivity Assay described in Example 3. Thallium-sensitive compounds typically have a large fluorescence intensity change at low thallium concentrations (e.g., concentrations of <4.5 mM). Thallium indicators having a fluorescence intensity change of 25% or more in the presence of thallium at a concentration of 5 mM or less are considered to be particularly sensitive to thallium and may be used in the assay methods described herein.

Various types of compounds have sensitivity to thallium and can be used in the practice of the invention. In one embodiment of the present invention, the thallium sensitive agent is a fluorescent compound (e.g., a fluorescent dye). Essentially any thallium-sensitive fluorescent compound that can be loaded into cells can be used. In one specific embodiment, the compound is selected to detect low concentrations of thallium ions (e.g., <4.5 mM). The compound may exhibit a change in one or more fluorescence properties upon association with thallium. For example, the fluorescence intensity of certain compounds may increase upon association with thallium. Alternatively, the fluorescence intensity of certain compounds may decrease upon association with thallium.

Association of thallium with a compound (e.g., fluorescent compound), as described herein, may occur by any means, with any portion of the compound, and by ionic or non-ionic interaction. In certain embodiments, the thallium indicator is a compound that binds to thallium (I) ions to produce a change in its fluorescence properties.

Any compound that exhibits a change in one or more of its fluorescence properties in response to binding of thallium may be used in the practice of the invention. Exemplary thallium indicators include fluorescent compounds based on xanthene. Xanthene-based compounds include, for example, fluorosceins or rhodols or rhodamines. In certain embodiments, the thallium indicator is a xanthene derivative. In other embodiments, the thallium indicator is a rhodol derivative. In other embodiments, the thallium indicator is a rhodamine derivative. Exemplary xanthene-based compounds, which may be used in the practice of the invention, include fluorosceins or rhodols substituted on one or more aromatic carbons by a halogen, such as, for example, fluorine. Exemplary fluorine-substituted xanthenes (e.g., fluorinated fluorescein and rhodal compounds) include those described in, for example, U.S. Pat. No. 6,162,931 and Gee et al., *Cell Calcium;* 2002, 31(5): 245-51. The following list provides particular examples of fluorinated xanthenes from which thallium indicators may be derived and which may be used according to the methods described herein:

6-amino-9-(2-carboxy-3,4,5,6-tetrafluorophenyl)-3H-xanthene-3-one,
6-amino-9-(2,4-dicarboxyphenyl)-2-fluoro-3H-xanthene-3-one,
6-amino-9-(2,4-dicarboxyphenyl)-7-fluoro-3H-xanthene-3-one,
4',5'-bis((di(carboxymethyl)amino)methyl)-2',7'-difluorofluorescein (2',7'-difluorocalcein),
4',5'-bis((di(carboxymethyl)amino)methyl)-2',7'-difluorofluorescein, acetoxymethyl ester (2',7'-difluorocalcein AM),
4-(carboxymethyl)thio-5,6,7-trifluorofluorescein,
6-(carboxymethyl)thio-4,5,7-trifluorofluorescein,
4-(carboxymethyl)thio-2',5,6,7,7'-pentafluorofluorescein,
6-(carboxymethyl)thio-2',4,5,7,7'-pentafluorofluorescein,
9-(4-carboxy-2-sulfophenyl)-2',7'-difluorofluorescein,
4',5'-dichloro-2',7'-dimethoxy-4,5,6,7-tetrafluorofluorescein-5-carboxylic acid,
2',7'-dichloro-4,5,6,7-tetrafluorofluorescein,
1',8'-difluorofluorescein,
2',7'-difluorofluorescein,
2',7'-difluorofluorescein diacetate,
4',5'-difluorofluorescein,
2',7'-difluoro-6-hydroxy-3H-xanthene-3-one,
2',7'-difluorofluorescein-5-carboxylic acid,
2',7'-difluorofluorescein-5-carboxylic acid diacetate,
2',7'-difluorofluorescein-5-carboxylic acid diacetate, acetoxymethyl ester,
2',7'-difluorofluorescein-6-carboxylic acid,
2',7'-difluorofluorescein-5-sulfonic acid,
2',7'-difluorofluorescein-6-sulfonic acid,
2',7'-dimethoxy-4,5,6,7-tetrafluorofluorescein,
2',7'-dimethoxy-4,5,6,7-tetrafluorofluorescein-5-carboxylic acid,
5-dodecanoylamino-2',7'-difluorofluorescein,
2'-fluorofluorescein,
4'-fluorofluorescein,
2',4,5,6,7,7'-hexafluorofluorescein,
2',4,5,6,7,7'-hexafluorofluorescein diacetate,
1,2,4,5,7,8-hexafluoro-6-hydroxy-9-(pentafluorophenyl)-3H-xanthene-3-one,
6-hydroxy-9-(2-sulfo-3,4,5,6-tetrafluorophenyl)-3H-xanthene-3-one,
2',4',5',7'-tetrabromo-4,5,6,7-tetrafluorofluorescein,
2',4',5',7'-tetrafluorofluorescein,
2',4',5',7'-tetrafluorofluorescein-5-carboxylic acid,
2',4',5',7'-tetrafluorofluorescein diacetate,
4,5,6,7-tetrafluorofluorescein,
4,5,6,7-tetrafluorofluorescein diacetate,
4,5,6,7-tetrafluorofluorescein-2',7'-dipropionic acid,
4,5,6,7-tetrafluorofluorescein-2',7'-dipropionic acid, acetoxymethyl ester, or
2',4',5',7'-tetraiodo-4,5,6,7-tetrafluorofluorescein.

Xanthene-based compounds having sensitivity to thallium also include commercially available compounds, such as FluoZin 1, FluoZin 2, FluoZin 3, Fluo-4FF, Magnesium Green, RhodZin-3, and Phen Green (all available from Invitrogen Corporation, Carlsbad, Calif.).

In another aspect, thallium indicators are provided which include a coumarin moiety. Representative examples of coumarin-based thallium indicators include, for example, BTC or a derivative thereof (e.g., APTRA-BTC).

In yet another aspect, thallium indicators are provided which include a benzofuran moiety. Representative examples of benzofuran-based thallium indicators include, for example, Mag-Fora Red or a derivative thereof (Invitrogen Corporation, Carlsbad, Calif.).

In yet another aspect, thallium indicators are provided which include a naphthalene moiety. Representative examples of naphthalene-based thallium indicators include, for example, ANTS (Invitrogen Corporation, Carlsbad, Calif.)

In yet another aspect, thallium indicators are provided which include a crown ether moiety. Representative examples of crown ether-based thallium indicators include, for example, PBFI (Invitrogen Corporation, Carlsbad, Calif.).

Although it is not required that thallium bind to a particular moiety or portion of the thallium indicator compound, particular thallium indicators of the invention may include an ion-complexing moiety. Representative examples of ion-complexing moieties include crown ethers, including diaryldiaza crown ethers; derivatives of 1,2-bis-(2-aminophenoxyethane)-N,N,N',N'-tetraacetic acid (BAPTA); derivatives of 2-carboxymethoxy-aniline-N,N-diacetic acid (APTRA); derivatives of 2-methoxy-aniline-N,N-diacetic acid, and pyridyl-based and phenanthroline metal ion chelators.

The thallium sensitive agents may be hydrophilic or hydrophobic. Any of the thallium sensitive compounds described herein, may be further derivatized to include a moiety that increases the hydrophilicity or hydrophobicity of the compound. For example, the compound may be derivatized to convert it to a more hydrophobic form, which may be able to more easily permeate cell membranes. For example, the thallium sensitive fluorescent agents can be loaded into the cell by contacting the cells with a loading buffer comprising the dye or a membrane-permeable derivative of the dye. Loading the cells with the dye may be further facilitated by using a more hydrophobic form of the dye.

For certain applications, it may be desired to provide a thallium indicator with a cleavable hydrophobic moiety. For example, thallium indicators with a cleavable hydrophobic moiety may readily enter the cell through the cell membrane. Once inside the cell, the moiety may be cleaved by an agent (e.g., enzyme) within the cell to produce a less hydrophobic compound, which remains trapped within the cell. The cleavable moiety may be any moiety susceptible to cleavage by an enzyme (e.g., esterases, lipases, phospholipases, and the like). Representative cleavable moieties include, for example, hydrophobic moieties, such acetoxymethyl (AM) ester. In some embodiments, a thallium indicator may be a dye in the form of an acetoxymethyl ester (AM), which is more hydrophobic in nature than the unmodified form of the dye, and is able to permeate cell membranes much more readily. As the acetoxymethyl ester form of the dye enters the cell, the ester group is removed by cytosolic esterases, thereby trapping the dye in the cytosol.

In certain embodiments, the thallium indicator is an AM ester derivative of a xanthene-based compound (e.g., a fluorinated xanthene, such as a fluorinated rhodol or fluoroscein). In certain embodiments, the thallium indicator is an AM ester derivative of a coumarin-based compound. In certain embodiments, the thallium indicator is an AM ester derivative of a benzofuran-based compound. In certain embodiments, the thallium indicator is an AM ester derivative of a naphthalene-based compound. In certain embodiments, the thallium indicator is an AM ester derivative of a crown-ether-based compound.

The thallium indicator may be in the form of a salt. "Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate. Representative examples of thallium indicator salts that may be used in the practice of the invention include those with a counterion, such as, for example, $Na^+$, $K^+$, $NH^{4+}$, and $NR^{4+}$. Salts of the compounds described herein may be prepared as salts using methods that are well known to those skilled in the art. It should also be understood that more than one thallium indicator (e.g., a combination of two or more thallium indicators) may be used in the practice of the invention.

The optical properties of the thallium indicators utilized in the present invention can be any optical property of the compound, provided that the property can change in response to thallium. Examples of optical properties of the luminescent (e.g., fluorescent) dyes include, but are not limited to intensity, frequency and polarity. In one specific embodiment, the intensity of the dye is detected or measured.

The fluorescence intensity of the thallium indicator may increase or decrease in the presence of thallium ions. Of the thallium sensitive fluorescent agents listed above (e.g., ANTS, Fluo-4, Fluo-3, PBFI, Phen Green, Magnesium Green, BTC, APTRA-BTC, Mag-Fura Red, Fluo-4FF, FluoZin-1 and FluoZin-2), ANTS, Fluo-4, Fluo-3, PBFI, Phen Green, APTRA-BTC and Mag-Fora Red demonstrate a decrease in fluorescence intensity in the presence of thallium ions. Magnesium Green, RhodZin-3, BTC, Fluo-4FF, FluoZin-1 and FluoZin-2 demonstrate an increase in fluorescence in the presence of thallium ions.

In one specific embodiment where a fluorescent thallium sensitive agent is used, the excess fluorescent compound can be removed by using a sufficient amount of an extracellular quencher. A "quencher," as used herein refers to a photon-reducing agent, which absorbs energy emitted by the fluorescent thallium indicator without reemitting fluorescence energy. The use of extracellular quencher removes the need to wash unloaded thallium sensitive fluorescent agent from the cells. The extracellular quenchers are not necessarily cell permeant and can be light absorbing fluorescent compounds having a fluorescence that can be easily separated from that of the thallium sensitive fluorescent agent. The absorption spectrum of the extracellular quenchers significantly absorbs the emission of the thallium sensitive fluorescent agent. The extracellular quenchers must be of a chemical composition that prevents their passage into the cells, and, generally speaking, the quenchers should be charged or very large compounds. The concentration range for extracellular quenchers may range from micromolar to millimolar concentrations, depending on their light absorbing properties. Types of extracellular quenchers that can be used include, but are not limited to, tartrazine and amaranth, acid red 37, congo red, trypan blue, brilliant black or a mixture of such quenchers. Quenchers are described in the Sigma-Aldrich Handbook of Dyes, Stains, and Indicators (Floyd G. Green, 1990, St. Louis, Mo., USA).

The invention also provides for the use of non-fluorescent agents that are sensitive to thallium concentrations. In one embodiment, the invention provides using a thallium sensitive agent which is a non-fluorescent compound that associates or reacts with thallium ion to form a product that can either form a precipitate or form a product that is colored, and thus cause detectable changes in the optical density of the test mixture. These compounds include but are not limited to, iodide, bromide, and chromate.

When the thallium sensitive agent is a non-fluorescent compound, absorbance can be recorded by, for example, a spectrophotometer, before, during, and after addition of thallium ions, and addition of channel modulators. The cells expressing ion channels and/or receptors are loaded with iodide, bromide or chromate ion. The cells are washed with, for example, a buffered saline solution. The transport of thallium into cells causes an increase or decrease in the optical density signal. Thallium ions pass through open channels down its concentration gradient and can result in changes in the optical density inside the cell, resulting in the recorded signals. Activation of the ion channel enhances the rate of influx of thallium ions, which can result, for example, in an increased formation of precipitant or colored product; inhibition decreases the rate of influx of thallium ions, which, can result, for example, in no or little change in precipitation or colored product formation. Generally the optical density remains the same if no thallium ions react with the non-fluorescent compound. Thus if the ion channel is blocked, and thallium ions influx is inhibited, little or no change in optical density is detected.

The loading buffer may also comprise chloride (e.g., chloride ions). In one embodiment of the present invention, the loading buffer comprises a detectable amount of chloride. In another embodiment, the loading buffer is chloride-free. In certain embodiments, the loading buffer is substantially free of chloride ions (e.g., less than 2 mM). In other embodiments, the loading buffer includes less than 1 mM chloride ions. One of the advantages that the present invention provides is to allow the use of chloride in the loading buffer and in the cell media, prior to stimulating the cells with thallium. In general, the source of chloride in buffers is usually from the NaCl or KCl salt, but the chloride can be from any source if present. The chloride, if present in the buffers, e.g., the loading buffer or the washing buffer, can be at virtually any concentration, since the methods of the present invention are not dependent upon the absence of chloride. Since chloride ions do not interfere with the assay, buffers containing physiological relevant concentrations of chloride can be used in the practice of the invention. "Physiological relevant concentration" refers to a concentration that is characteristic of or consistent with an organism's healthy or normal functioning. In certain embodiments, the chloride concencentration of the loading solution is greater than about 2 mM. In certain embodiments, the chloride concencentration of the loading solution is greater than about 5 mM. In certain embodiments, the chloride concencentration of the loading solution is greater than about 10 mM. In other embodiments, the chloride concentration of the loading solution is about 5 mM to about 20 mM. In yet other embodiments, the chloride concencentration of the loading solution is greater than about 20 mM to about 100 mM. In yet other embodiments, the chloride concencentration of the loading solution is about 50 mM to about 150 mM. In some embodiments, the loading buffer comprises chloride that is at a concentration of about 10 mM, to about 150 mM. In other embodiments, the loading buffer comprises chloride at a concentration of about 50 mM to about 150 mM. In other embodiments, the loading buffer comprises chloride at a concentration of about 75 mM to about 125 mM. In other embodiments, the loading buffer comprises chloride at a concentration of about 100 mM to about 125 mM. Other concentrations of chloride may also be used, where one of skill in the art can readily determine the levels of chloride that are acceptable.

After the loading buffer is provided to the cells, the stimulus buffer is added to the cells to stimulate thallium movement into or out of the cells. The stimulus buffer should comprise thallium.

A stimulus buffer is a solution that activates the ion channel, channel-linked receptor or ion transporter (e.g., agonist). Some ion channels/transporters may be constitutively active and thus would not require a "stimulus" in addition to the thallium ion tracer. For channels that require a stimulus, that stimulus may be ligand (a molecule that binds to the channel or channel linked receptor and activates the same (an agonist). A stimulus might also be a change in membrane potential for voltage-gated channels. Typically voltage-gated channels are activated by either direct electrical stimulation with electrodes or by using a stimulus solution that contains an ionic composition that will cause depolarization (such as high external potassium). In addition, thallium ions can also act as a stimulus for voltage-gated channels. In such a case, thallium ions can act as both a "tracer" and a depolarizing stimulus. In an influx assay, thallium ions can be added just before, during, or after the addition of a stimulus.

The methods of the present invention can use stimulus buffers that are selected based on the type of ion channel, channel-linked receptor or ion transporter used in the method. Selecting an appropriate stimulus solution and ion channel, channel-linked receptor or ion transporter-activating reagent, is within the skill of the art. In one embodiment, the stimulus buffers include a buffer that does not include reagents that activate the ion channel, such that the ion channels, the channel-linked receptors or the ion transporters remain substantially at rest. In this embodiment, the stimulus solution includes reagents that do not activate the ion channel, channel-linked receptor or ion transporter of interest but facilitate activation of ion channel, channel-linked receptor or ion transporter when a modulating reagent is added to the cells to initiate the assay.

The stimulus solution selected for use with voltage-dependent ion channels, e.g., the N-type calcium channel or KCNQ2 channel, depends upon the sensitivity of the ion channel to the resting potential of the cell membrane. For methods using these voltage-dependent ion channels, the stimulating solution may include activating reagents that serve to depolarize the membrane, e.g., ionophores, valinomycin, etc.

A stimulus buffer selected for use with some voltage-dependent ion channels for activation by depolarization of the cell membrane includes potassium salt at a concentration such that the final concentration of potassium ions in the cell-containing well is in the range of about 10-150 mM, e.g., 50 mM KCl. In addition, voltage-dependent ion channels may also be stimulated by an electrical or light activated stimulus, such as is the case with light excitation of quantum dot nanocrystals or light sensitive ion channels expressed on the cell's surface.

The stimulus buffer selected for use with channel-linked receptors and ligand-gated ion channels depends upon ligands that are known to activate such receptors. For example, nicotinic acetylcholine receptors are known to be activated by nicotine or acetylcholine; similarly, muscarinic acetyl choline receptors may be activated by addition of muscarine or carbamylcholine. The stimulating buffer for use with these systems may include nicotine, acetylcholine, muscarine or carbamylcholine. In certain embodiments, the stimulus is an agonist of a G-protein coupled receptor that is capable of activating GIRK potassium ion channels to allow thallium influx. In other embodiments, the stimulus buffer may include a composition that will cause depolarization of the ion channel. A depolarizing composition may include, for example, agents such as ionophores, valinocmycin, or potassium salts. Depolarization of cell membranes may be achieved using light activated ion channels on the cell surface, such as channel rhodopsin or halorhodopsin, or light activated quantum dot nanocrystals.

Thallium in the stimulus buffer can be in any form, but it will primarily be in the form of a salt, thus providing thallium ions. In certain embodiments, the source of thallium is a salt. The thallium salts for use in thallium solutions used in the methods of the invention include those that are water soluble, such as but not limited to, $Tl_2SO_4$, $Tl_2CO_3$, TlCl, TlOH, TlOAc, $TlNO_3$ salts and the like. In certain embodiments, the thallium salt is soluble in the loading buffer solution.

The thallium in the stimulus buffer can be at a very low concentration, since the thallium indicators of the invention are sensitive to very low concentrations of thallium. Since thallium may be present in a low concentration, thallium ions can remain soluble in the buffers, described herein, regardless of the concentration of chloride. Generally, the thallium (e.g., thallium ions) in the stimulus buffer is at a concentration of less than about 4.5 mM. In certain embodiments, the thallium concentration may be less than about 4.0 mM. In other embodiments, the thallium concentration may be less than about 3.0 mM. In other embodiments, the thallium concentration may be 2.5 mM or less. In certain embodiments, the concentration of thallium (e.g., thallium ions) may be about 0.1 mM to about 2 mM and the loading buffer comprises chloride ions at a concentration of about 10 mM to about 150 mM. In certain embodiments, the concentration of thallium (e.g., thallium ions) may be about 0.1 mM to about 4 mM and the loading buffer comprises chloride ions at a concentration of about 10 mM to about 150 mM. Certain methods of the invention utilize a stimulus buffer with thallium at a concentration of about 1 mM to about 10 mM and a loading buffer that includes chloride ions at a concentration of about 10 mM to about 150 mM. In other embodiments, the concentration of thallium may be about 2 mM to about 5 mM and the loading buffer comprises chloride ions at a concentration of about 10 mM to about 150 mM. In other embodiments, thallium is at a concentration of about 5 mM to about 20 mM and the loading buffer comprises chloride ions at a concentration of about 10 mM to about 150 mM. In other separate embodiments, the loading buffer comprises chloride ions at a concentration of about 50 mM to about 150 mM, and the concentration of thallium (e.g., thallium ions) may be about 0.1 mM to about 2 mM; or about 0.1 mM to about 4.0 mM; or about 1 mM to about 10 mM; or about 2 mM to about 5 mM; or about 5 mM to about 20 mM. Other concentrations of thallium and chloride may also be used in the methods of the invention.

In another aspect, solutions are provided that include a thallium indicator, a loading buffer comprising a thallium indicator and a physiological concentration of chloride ions, and thallium (e.g., thallium ions). The thallium concentration in the solution is typically <4.0 mM, but the solution may include higher levels of thallium, as well. For example, the thallium concentration of the solution may range from about 0.1 mM to about 20 mM. For example, the thallium concentration of the solution may be about 0.1 mM to about 2 mM; or about 0.1 mM to about 4.0 mM; or about 1 mM to about 10 mM; or about 2 mM to about 5 mM; or about 5 mM to about 20 mM. The chloride concentration of the solution may be about 150 mM or less and may range from about 10 mM to about 150 mM; or about 50 mM to about 150 mM; or about 100 mM to about 150 mM. In one embodiment, the thallium concentration is less than 4.0 mM and the chloride ion concentration is 50 mM to about 150 mM. The thallium indicator is present in the solution in an amount to be sufficient to detect the presence of thallium ions.

The transport of thallium sensitive agents and thallium ions into cells is followed by an increase or decrease in the signal of the environmentally sensitive agent. Thallium ions move through open channels along their concentration gradient and change the intensity of dye fluorescence inside the cell, resulting in the recorded signals. Activation of the ion channel enhances the rate of influx of thallium ions (resulting in a change in the fluorescence of the thallium sensitive fluorescent compound) and inhibition decreases the rate of influx of thallium ions (resulting in no or little change in the fluorescence of the thallium sensitive fluorescent agent). Generally the fluorescence remains the same if no thallium ion is bound to it.

At least one optical property of the environmentally sensitive agent is detected or measured in the methods of the present invention. As mentioned earlier, if fluorescent dyes are utilized, any optical property of the fluorescent dye can be measured or detected to determine thallium influx or efflux. Examples of optical properties of fluorescent dyes include, but are not limited to, intensity, polarity and frequency of the luminescence of the fluorescent dyes. If non-fluorescent dyes are used as the detecting agent, the optical properties of the agent to be detected can be also be intensity, polarity and frequency. In one specific aspect of the present invention, measuring or detecting the optical properties of the agent includes measuring the optical density of the cells themselves, when, for example, the agent reacts with thallium to form a product or precipitant within the cell itself that may increase the optical density of the cell itself.

If fluorescent dyes are used, the fluorescence of the thallium sensitive agent can be measured by devices that detect fluorescent signals, such as but not limited to spectrophotometers, microscopes and the like. In one specific embodiment, the fluorescence of the dyes is detected and/or measured using a standard 96-well plate reader. Another type of device is a fluorescent imaging plate readers, such as the FLIPR device (Molecular Devices Corp., Sunnyvale, Calif.), where fluorescence is recorded at a rate of up to 1 Hz, before, during, and after addition of thallium ions, and addition of candidate ion channel, channel-linked receptor or ion transporter modulators. Examples of devices used for non-adherent cells include FLIPR devices and flow cytometers (Becton-Dickinson). Still more examples of devices and methods used to detect or measure the optical properties of the agents include, but are not limited to, light microscopy, confocal microscopy, and fluorescence microscopy.

In one embodiment of the present invention, the activity of channel-linked receptors is determined, where the activation of the receptor initiates subsequent intracellular events that lead to the modulation of ion channel activity.

The invention also provides methods for identifying compounds that modulate ion channel, channel-linked receptor, or ion transporter activity. Essentially any chemical compound can be used as a potential modulator in the assays of the invention. In specific embodiments, the candidate compounds can be dissolved in aqueous or organic (e.g., DMSO-based) solutions. It will be appreciated by those of skill in the art that there are many commercial suppliers of chemical compounds, including Sigma Chemical Co. (St. Louis, Mo.), Aldrich Chemical Co. (St. Louis, Mo.), Sigma-Aldrich (St. Louis, Mo.), Fluka Chemika-Biochemica Analytika (Buchs, Switzerland), and the like. Thus if the ion channel is blocked by the candidate channel modulator and thallium influx is inhibited, little or no change in fluorescence will be detected.

The present invention also provides methods for detecting the efflux of thallium through an ion channel. In general, methods to evaluate thallium efflux involve loading a cell that includes an ion channel with thallium using methods that are known to those skilled in the art. For example, a cell may be combined with a solution (e.g., buffer) containing thallium (e.g., thallium salt) and incubated for a time sufficient to load the cells with thallium. The thallium-loaded cells can, optionally, be washed to remove excess thallium. A solution that includes a thallium indicator and a physiological concentration of chloride ions then is added to the cell and the ion channel of the cell is stimulated, such as to cause flux of thallium through the ion channel. A thallium indicator that is impermeable to the ion channel may be used, such that the indicator does not pass into the cell. Detection of the thallium indicator upon stimulation of the cell provides information about the activity of the ion channel. In certain embodiments, an optical property of the thallium indicator is detected.

The efflux assays can use the same cells as in the influx assays, and are loaded with a signal generating thallium sensitive fluorescent agent, as described herein, such as BTC. Additional examples of indicators that may be used in the described efflux assays include, without limitation, Magnesium Green, Fluo-4FF, FluoZin-1 or FluoZin-2, RhodZin-3, ANTS, Fluo-4, Fluo-3, PBFI, Phen Green, or Mag-Fora Red or a derivative or salt thereof. The cells are contacted with thallium to load the cells. One embodiment provides contacting the cells with thallium ions for approximately 15 minutes. The cells can be washed to remove excess thallium ions and assayed using the same instrument to detect changes in signal as used in the influx assay, e.g., the Fluorometric Image Plate Reader (FLIPR) (Molecular Devices Corp., Sunnyvale, Calif., USA.). The assay channels are stimulated to open by the addition of any one of a number of ligands, or by changing the membrane potential of the cell, such as by changing the potassium concentrations, to permit efflux of ions through the ion channels. For example, an efflux would result in a decrease in fluorescence of BTC. The other compounds, such as control compounds, can be the same as used in the influx assays. The same conditions are applied as for the influx assay in the methods of the invention, except the cells are preloaded with thallium ions as described above, and washed to remove excess thallium ions.

In the thallium influx and efflux assays provided herein, the thallium indicator may be any of compounds described herein. In certain embodiments, a thallium indicator is a fluorescent compound that exhibits a fluorescence intensity change of 25% or greater in the Thallium Sensitivity Assay, described in Example 3. Certain thallium indicators sensitive to monovalent and divalent cations (e.g., $Zn^{2+}$ or $Ca^{2+}$) test positive in the Thallium Sensitivity Assay and are particularly useful in the fluorescence-based thallium influx and efflux assays of the invention. Representative examples of such fluorescent thallium indicators include compounds with a xanthene moiety (e.g., FluoZin 1, FluoZin 2, FluoZin 3, FluoZin 4, Red Fluo-4FF, Magnesium Green, Phen Green, RhodZin-3, or a derivative or salt thereof); a benzofuran moiety, such as Mag-Fura Red or a derivative or salt thereof; a naphthalene moiety (e.g., ANTS), or a crown ether moiety (e.g., PBFI). Fluorescent xanthine, benzofuran, naphthalene, and crown-ether-based compounds substituted with an acetoxymethyl ester moiety may be used under certain circumstances (e.g., to retain the compound within the cell). Depending on the form of thallium and the amount of chloride ions present, it may be desired to use a fluorescent thallium indicator that includes a coumarin moiety (e.g., BTC or APTRA-BTC or a derivative or salt thereof).

In one aspect, methods are provided for detecting the activity of an ion channel in a cell, the method comprising: a) providing a cell with an ion channel; b) providing a loading buffer solution to the cell, the loading buffer solution comprising a thallium indicator and a physiological concentration of chloride ions (e.g., about 50 mM to about 150 mM); c) providing a stimulus buffer to the cell, wherein the stimulus buffer comprises thallium, and wherein providing the stimulus buffer causes thallium influx into the cell through the ion channel; and d) detecting the thallium indicator. The thallium concentration may be less than about 4.5 mM. The thallium indicator used in the method may be a fluorescent compound comprising a xanthene moiety (e.g., FluoZin 1, FluoZin 2, FluoZin 3, FluoZin 4, Red Fluo-4FF, Magnesium Green, Phen Green, RhodZin-3, or a derivative or salt thereof). Alternatively, the thallium indicator may be a fluorescent compound comprising a benzofuran moiety, such as Mag-Fura Red or a derivative or salt thereof; a naphthalene moiety (e.g., ANTS), or a crown ether moiety (e.g., PBFI).

In another aspect, methods are provided for detecting the activity of an ion channel in a cell, the method comprising: a) loading a cell with thallium, wherein the cell comprises an ion channel; b) providing a solution to the cell, the solution comprising a thallium indicator and a physiological concentration of chloride ions (e.g., about 50 mM to about 150 mM); c) stimulating the ion channel of the cell, such as to cause efflux of thallium through the ion channel; and d) detecting the thallium indicator. The thallium concentration in the cell after loading may be less than about 4.5 mM. The thallium indicator used in the method may be a fluorescent compound comprising a xanthene moiety (e.g., FluoZin 1, FluoZin 2, FluoZin 3, FluoZin 4, Red Fluo-4FF, Magnesium Green, Phen Green, RhodZin-3, or a derivative or salt thereof). Alternatively, the thallium indicator may be a fluorescent compound comprising a benzofuran moiety, such as Mag-Fura Red or a derivative or salt thereof; a naphthalene moiety (e.g., ANTS), or a crown ether moiety (e.g., PBFI).

The methods of the present invention can also be adapted to high-throughput screening methods, such that candidate ion channel modulators can be screened on a large scale. High-throughput screening assays are known, and employ the used of microtiter plates or pico-nano- or micro-liter arrays.

The high-throughput methods of the invention can be performed using whole cells expressing ion channels, ion channel and channel-linked receptors or ion transporters of interest, by practicing the methods of the present invention on microtiter plates or the like. The cells can be cultured under adherent or non-adherent conditions. The target compounds are added to the cells as a pre-treatment and then the stimulus buffer(s) are added to the cells and, for example, fluorescence is detected. The change in the detectable signal would indicate the effect of the channel modulators in a particular well on a plate.

The assays of the invention are designed to permit high throughput screening of large chemical libraries, e.g., by automating the assay steps and providing candidate modulatory compounds from any convenient source to assay. Assays which are run in parallel on a solid support, e.g., microtiter formats on microtiter plates in robotic assays, are well known. Automated systems and methods for detecting and/or measuring changes in optical detection are also well known (U.S. Pat. Nos. 6,171,780; 5,985,214; and 6,057,114).

The high throughput screening methods of the invention include providing a combinatorial library containing a large number of potential therapeutic modulating compounds (Borman, S, C. & E. News, 1999, 70(10), 33-48). Preparation and screening of combinatorial chemical libraries is well known to those of skill in the art.

A combinatorial chemical library is a collection of diverse chemical compounds generated by using either chemical synthesis or biological synthesis, to combine a number of chemical building blocks, such as reagents. For example, a linear combinatorial chemical library, such as a polypeptide library, is formed by combining a set of amino acids in virtually every possible way for a given compound length, i.e., the number of amino acids in a polypeptide compound. Millions of chemical compounds can be synthesized through such combinatorial mixing of chemical building blocks.

Also provided by the present invention are kits for detecting the activity of ion channels in a cell. In one particular embodiment, the kits comprise the dye, the assay buffer, which may include chloride, and the stimulus buffer. The individual components of the buffers and the dyes may be lyophilized or stored in some other dehydrated form, where the individual can hydrate the components into stock or working solutions. The kits of the invention may contain virtually any combination of the components set out above or described elsewhere herein. One exemplary kit for detecting the activity of an ion channel (e.g., thallium influx) in a cell includes: a) a loading buffer solution that includes a thallium indicator and a physiological concentration of chloride ions; and b) a stimulus buffer that includes thallium, wherein the stimulus buffer causes thallium influx into the cell through the ion channel. Another exemplary kit for detecting the activity of an ion channel (e.g., thallium efflux) in a cell includes: a) a thallium loading solution that includes thallium (e.g., thallium ions; and b) a solution (e.g., buffer solution) that includes a thallium indicator and a physiological concentration of chloride ions. As one skilled in the art would recognize, the components supplied with kits of the invention will vary with the intended use for the kits. Thus, kits may be designed to perform various functions set out in this application and the components of such kits will vary accordingly.

A detailed description of the invention having been provided above, the following examples are given for the purpose of illustrating the invention and shall not be construed as being a limitation on the scope of the invention or claims.

EXAMPLES

Example 1

Thallium Influx Assay

The following is in example of the components that may be used in some of the methods of the present invention.

Component A:

Per Vial: FluoZin-1 AM ester (Invitrogen) 1-20 μg

Lyophilized and stored in a single use 15 mL vial

Component B: 5× Assay Buffer: 1×25 mL

| Per Vial: | 50% Vol 10X HBSS | 12.5 mL |
| --- | --- | --- |
| | 10% Vol 1M HEPES | 2.5 mL |
| | 40% Vol H$_2$O | 10 mL |

Component C: 5× Chloride Free Stimulus Buffer: 1×25 mL

| Per vial: | 700 mM Na Gluconate | 3.82 g |
| --- | --- | --- |
| | 12.5 mM K Gluconate | 73 mg |
| | 9 mM Ca Gluconate | 96.7 mg |
| | 5 mM Mg Gluconate | 51.7 mg |
| | 100 mM HEPES | 2.5 mL 1M |
| | Water | 22.5 mL |

Component D: Concentrated (125 mM) K$_2$SO$_4$ Solution: 1×20 mL

| Per vial | 125 mM Potassium Sulfate | 435 mg |
| --- | --- | --- |
| | H$_2$O | 20 mL |

Component E: Concentrated (50 mM) Tl$_2$SO$_4$ Solution: 1×20 mL

| Per vial | 50 mM Thallium Sulfate | 505 mg |
| --- | --- | --- |
| | H$_2$O | 20 mL |

Component F: 100×: 1×1 mL

| Per vial | PLURONIC F127 | 20-100 mg |
| --- | --- | --- |
| | PLURONIC P85 | 5-20 mg |
| | H$_2$O | 1 mL |

Cells comprising an ion channel are cultured to about 75% confluence and in log-phase growth. The cells are then harvested using well-known cell culture techniques and buffers and replated into a 96-well plate at a density of, for example, 2×10$^5$ cells/well. The cells can comprise the ion channel endogenously, or the cells can be engineered to comprise ion channels of a particular type. Methods of transfecting and/or transforming cells to express a particular type of protein are well known in the art and need not be repeated herein.

To prepare the loading buffer, a vial of component A is warmed to room temperature, 100 uL Component F is added to the loading buffer to solublize and carry the dye into the cells across the plasma membrane. After swirling the above mixture, 2 mL of component B, 5×HBSS (Hank's Buffered Salt Solution) is added, followed by 8 mL H$_2$O.

Next the cell culture media is aspirated from the cells in the 96 well plate and replaced with 100 μL loading buffer per well. Media left behind in the wells will promote hydrolysis of the dye before it enters the cells.

After loading, the microplate is covered from direct light and incubated at room temperature for 60-120 minutes. Best comparisons will be made between plated assayed after similar times in loading buffer.

While the cells are incubating, a stimulus buffer containing 25 mM K$_2$SO$_4$ and 10 mM Tl$_2$SO$_4$, is prepared according to the following: 2 mL H$_2$O is combined with 1 mL Component C (5× Chloride Free Buffer), 1 mL Component D (125 mM K$_2$SO$_4$), 1 mL Component E (50 mM Tl$_2$SO$_4$). This formulation will yield a stimulus buffer that dilutes into the microplate at 1:5, yielding final concentrations of 10 mM free potassium ion and 4 mM free thallium (I) ion.

Next, a "compound plate" is and set up and the assay is run. First, the stimulus buffer is poured into a trough for dispensing into the compound plate. Using an 8 channel pipettor, 150 ul of the stimulus buffer is added per compound plate column for coverage of 4 microplate columns at 25 uL per dispense. Optionally, the cells can be washed after the stimulus buffer is added to remove the extracellular thallium. The methods of the present invention, however, can be performed with or without a washing step to remove the excess thallium.

Next, the fluorescence is read on a spectrophotometer. The sample is excited with light at 488 nm, and emission is read at 525 nm, with a filter cutoff of 515 nm. The time for reading is set for anywhere between 90-300 seconds, with 5 second interval readings.

Example 2

Assay of Cells Transfected with hERG Ion Channels

Figure 1:
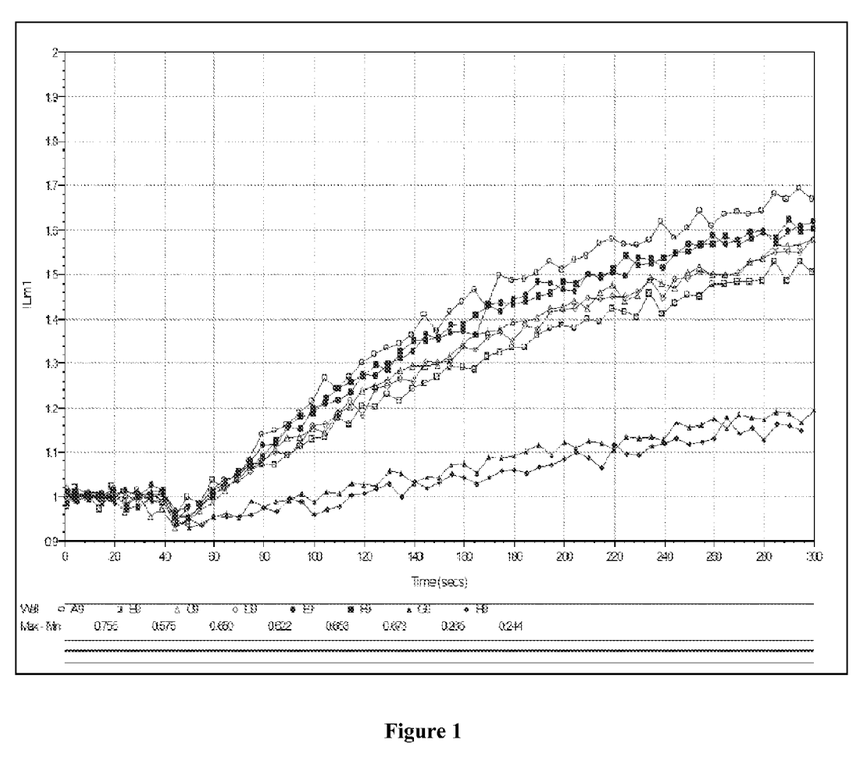
FIG. 1 depicts thallium influx of cells transfected with the hERG potassium ion channel gene under control of the tetracycline inducible promoter. Cells that were transfected with the hERG gene and induced with tetracycline to promote expression of the hERG gene demonstrated thallium influx. Transfected cells that were not induced did not demonstrate thallium influx (bottom curves).
Figure 2:
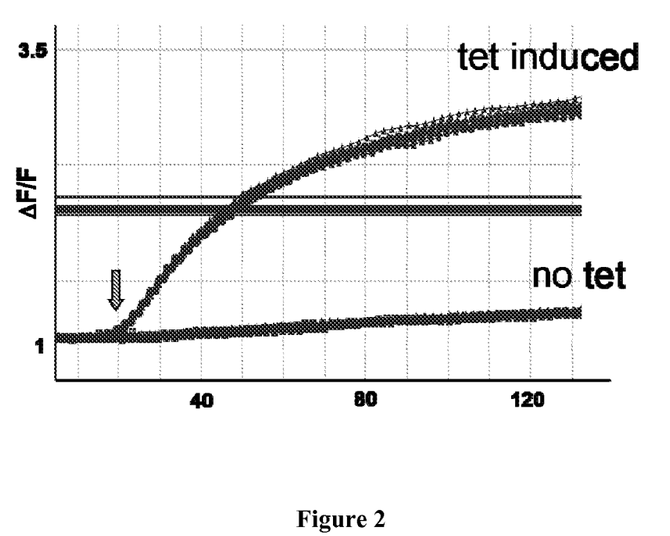
FIG. 2 depicts hERG activity measured in a 96 well plate with the FLUXOR Thallium NW Detection Kit (Invitrogen Corporation, Carlsbad, Calif.).

Cells transfected with the hERG ion channels were assayed using the methods of the present invention. Cells were loaded in assay buffer containing 0.5 uM FluoZin-1 AM ester and stimulated with 1× dilution of stimulus buffer (Component C, containing 25 mM K$_2$SO$_4$ and 10 mM Tl$_2$SO$_4$). "Control" were tet-stimulated hERG 293 T Rex cells, and "no tet" traces were cells which were not stimulated to express hERG. The stimulus was delivered to the cells in a volume of 25 uL, added to 100 uL for a 5× dilution. In this particular example, the final concentration of thallium on the cells was about 4 mM. FIG. 1 demonstrates the absorbance curves of cells (plotted as dF/F as a function of time) transfected with the hERG ion channel and assayed using the methods of the present invention. FIG. 2 depicts hERG activity cells transfected with hERG ion channels (tetracycline induced and non-tetracycline induced) measured in a 96 well plate with the FLUXOR Thallium NW Detection Kit (Invitrogen Corporation, Carlsbad, Calif.) (time of potassium ion stimuluation shown by arrow).

Example 3

Thallium Sensitivity Assay

An assay is provided to evaluate a compound's sensitivity to thallium (I). Compounds with sufficient sensitivity to thallium (I) may be used as thallium indicators for measuring thallium influx and efflux through ion channels. A 10 micromolar solution of a fluorescent compound is prepared in 10 mM HEPES buffer, pH 7.4. The maximum fluorescence emission intensity is measured by excitation at the compound's excitation maximum wavelength. The measurement is performed in a cuvette in spectrofluorimeter or in a microplate well in a fluorescence microplate reader. Increasing amounts of a stock aqueous solution of thallium sulfate are added to the fluorescent compound solution, such that the final concentration of thallium (I) is 0, 5, 10, 50, 100, 500, 1000, and 2000 micromolar. After each addition of thallium sulfate solution, the fluorescence intensity is measured and compared with the intensity obtained in the presence of zero thallium (I). An overall fluorescence intensity change of 25% or greater through the range of thallium (I) concentrations indicates that the compound has sufficient thallium (I) sensitivity to be further evaluated in assays for measuring thallium influx and efflux through ion channels.

All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for detecting the activity of potassium ion channel in a cell, the method comprising:
providing a loading buffer solution to the cell, the loading buffer solution comprising a thallium indicator and a physiological concentration of chloride ions, wherein the thallium indicator is an acetoxymethyl ester of a xanthene-based compound comprising a thallium ion-complexing moiety, wherein the thallium ion-complexing moiety is 2-methoxy-aniline-N,N-diacetic acid or a derivative thereof, and wherein the chloride ions are at a concentration of about 50 mM to about 150 mM;
providing a stimulus buffer to the cell, wherein the stimulus buffer comprises thallium at a concentration of about 0.1 mM to about 5.0 mM, thereby causing thallium influx into the cell through the potassium ion channel; and
measuring a change in at least one optical property of the thallium indicator in response to thalium influx thereby detecting the activity of the potassium ion channel.

2. The method of claim 1, wherein the thallium indicator associates with thallium within the cell.

3. The method of claim 1, wherein the thallium indicator is a compound that exhibits an increase in fluorescence when associated with a thallium ion.

4. The method of claim 1, wherein the thallium indicator is a compound that exhibits a change in the optical density inside the cell when associated with a thallium ion.

5. The method of claim 1, wherein the thallium indicator exhibits a decrease in fluorescence intensity in the presence of thallium ions.

6. The method of claim 1, wherein the thallium indicator exhibits an increase in fluorescence in the presence of thallium ions.

7. The method of claim 1, wherein the thallium indicator is a fluorescent compound that is sensitive to monovalent or divalent cations.

8. The method of claim 7, wherein the thallium indicator is a $Zn^{2+}$ or $Ca^{2+}$ indicator.

9. The method of claim 1, wherein the thallium indicator is FluoZin 1, FluoZin 2, or a derivative or salt thereof.

10. The method of claim 1, wherein the thallium is in the form or a salt.

11. The method of claim 10, wherein the thallium salt is soluble in the loading buffer solution.

12. The method of claim 10, wherein the thallium salt is selected from $Tl_2SO_4$, $Tl_2CO_3$, TlCl, TlOH, TlOAc, and $TlNO_3$.

13. The method of claim 1, further comprising quantifying the level of thallium, or washing the cells after the loading buffer solution is provided to the cells.

14. The method of claim 1, wherein the at least one optical property of the thallium indicator is intensity, polarity, frequency, or optical density.

15. The method of claim 1, wherein the change in the at least one optical property of the thallium indicator is measured by light microscopy, confocal microscopy, fluorescence microscopy or spectrophotometry.

16. The method of claim 1, further comprising adding a quencher to the loading buffer solution.

17. The method of claim 16, wherein the quencher is substantially not cell permeant.

18. The method of claim 17, wherein the quencher is tartrazine, amaranth, acid red 37, congo red, trypan blue, brilliant black, or a combination thereof.

19. The method of claim 1, further comprising stimulating the ion channel with a stimulus.

20. The method of claim 19, wherein the stimulus is a ligand that binds to the ion channel, a channel-linked receptor, or an electrical stimulus.

21. The method of claim 19, wherein the stimulus is a G-protein coupled receptor agonist capable of activating activate GIRK potassium ion channels to allow thallium influx.

22. The method of claim 19, wherein the stimulus is nicotine, acetylchloline, muscarine, carbamyline, or a GIRK potassium ion channel activator.

23. The method of claim 19, wherein the stimulus comprises a composition that causes depolarization of the ion channel.

24. The method of claim 23, wherein the composition comprises ionophores, valinocmycin, or potassium salts.

25. The method of claim 23, wherein the composition comprises channel rhodopsin, halorhodopsin, or quantum dot nanocrystals.

26. The method of claim 1, wherein the stimulus buffer comprises thallium at a concentration of about 0.1 mM to about 4.0 mM.

27. The method of claim 1, wherein the method does not comprise washing the cells after the loading buffer is provided to the cells.

28. The method of claim 1, wherein the cell is selected from the group consisting of bacterial, yeast, plant, and animal cells.

29. The method of claim 28, wherein the animal cells is a mammalian cell selected from the group consisting of a neuron, cardiac cell, cancer cell, smooth muscle cell and an immortalized cell.

30. The method of claim 1, wherein the xanthene-based compound is substituted on one or more aromatic carbons by fluorine.

* * * * *

UNITED STATES PATENT AND TRADEMARK OFFICE
CERTIFICATE OF CORRECTION

| | |
|---|---|
| PATENT NO. | : 9,476,892 B2 |
| APPLICATION NO. | : 14/521346 |
| DATED | : October 25, 2016 |
| INVENTOR(S) | : Daniel Beacham and Kyle Gee |

It is certified that error appears in the above-identified patent and that said Letters Patent is hereby corrected as shown below:

In Claim 1, at Column 21, Line 57, delete "of potassium" and insert --of a potassium-- therefor.

In Claim 10, at Column 22, Line 32, delete "or a" and insert --of a-- therefor.

In Claim 29, at Column 23, Line 18, delete "cells" and insert --cell-- therefor.

Signed and Sealed this
Second Day of May, 2017

Michelle K. Lee
*Director of the United States Patent and Trademark Office*